United States Patent
Foley

(10) Patent No.: US 6,951,533 B2
(45) Date of Patent: Oct. 4, 2005

(54) ORGAN MANIPULATION ASSISTANCE DURING SURGICAL PROCEDURE

(75) Inventor: Frederick J. Foley, Bedford, NH (US)

(73) Assignee: Iotek, Inc., Minneapolis, MN (US)

( * ) Notice: Subject to any disclaimer, the term of this patent is extended or adjusted under 35 U.S.C. 154(b) by 0 days.

(21) Appl. No.: 10/067,097

(22) Filed: Feb. 4, 2002

(65) Prior Publication Data

US 2003/0149336 A1 Aug. 7, 2003

(51) Int. Cl.$^7$ .................................................. A61F 2/00
(52) U.S. Cl. ........................................................ 600/37
(58) Field of Search ............................ 600/16, 18, 37, 600/204–208, 201, 210, 219, 235, 17; 128/898, 897, 242, 44, 158–162, 64; 601/153, 6, 41; 606/151, 1, 205, 206, 193, 123, 166, 213; 623/3.1

(56) References Cited

U.S. PATENT DOCUMENTS

| | | | | |
|---|---|---|---|---|
| 3,983,863 A | | 10/1976 | Janke et al. | |
| 4,048,990 A | * | 9/1977 | Goetz | 601/153 |
| 4,428,375 A | * | 1/1984 | Ellman | 606/151 |
| 4,973,300 A | | 11/1990 | Wright | |
| 4,991,574 A | | 2/1991 | Pocknell | |
| 5,119,804 A | * | 6/1992 | Anstadt | 601/153 |
| 5,131,905 A | * | 7/1992 | Grooters | 600/16 |
| 5,150,706 A | | 9/1992 | Cox et al. | |
| 5,256,132 A | * | 10/1993 | Snyders | 600/16 |
| 5,279,539 A | | 1/1994 | Bohan et al. | |
| 5,509,890 A | | 4/1996 | Kazama | |
| 5,571,074 A | * | 11/1996 | Buckman et al. | 601/6 |
| 5,702,343 A | * | 12/1997 | Alferness | 600/37 |
| 5,727,569 A | * | 3/1998 | Benetti et al. | 128/898 |
| 5,738,627 A | * | 4/1998 | Kovacs et al. | 600/16 |
| 5,749,839 A | * | 5/1998 | Kovacs | 601/153 |
| 5,957,977 A | * | 9/1999 | Melvin | 623/3.1 |
| 6,155,972 A | | 12/2000 | Nauertz et al. | |
| 6,169,922 B1 | | 1/2001 | Alferness et al. | |
| 6,174,279 B1 | | 1/2001 | Girard | |
| 6,193,648 B1 | | 2/2001 | Krueger | |
| 6,251,065 B1 | | 6/2001 | Kochamba et al. | |
| 6,258,023 B1 | | 7/2001 | Rogers et al. | |
| 6,290,644 B1 | | 9/2001 | Green, II et al. | |
| 6,293,906 B1 | | 9/2001 | Vanden Hoek et al. | |
| 6,306,085 B1 | | 10/2001 | Farascioni | |
| 6,315,717 B1 | | 11/2001 | Benetti et al. | |
| 6,390,976 B1 | | 5/2002 | Spence et al. | |
| 6,517,563 B1 | | 2/2003 | Paolitto et al. | |
| 6,558,314 B1 | * | 5/2003 | Adelman et al. | 600/37 |
| 6,612,979 B2 | * | 9/2003 | Lau et al. | 600/37 |
| 6,656,109 B2 | | 12/2003 | DeVries et al. | |

FOREIGN PATENT DOCUMENTS

DE 199 47 885 4/2000

\* cited by examiner

*Primary Examiner*—Eric F. Winakur
*Assistant Examiner*—Nikita R. Veniaminov
(74) *Attorney, Agent, or Firm*—Shumaker & Sieffert, PA

(57) ABSTRACT

The invention provides techniques for securely engaging an organ, such as a beating heart, with a manipulating device. A bag-like device may be deployed around a substantial volume of the organ and the manipulating device. In one embodiment, the bag-like device may be net-like, including one or more mesh apertures. Once deployed, the bag-like device cooperates with the manipulating device when the organ is manipulated and reduces the risk that the organ will be inadvertently released or dropped.

27 Claims, 4 Drawing Sheets

ORGAN MANIPULATION ASSISTANCE DURING SURGICAL PROCEDURE

TECHNICAL FIELD

The invention relates to devices capable of providing adherence to organs of the body for purposes of medical diagnosis and treatment. More particularly, the invention relates to devices capable of adhering to, holding, moving, stabilizing or immobilizing an organ.

BACKGROUND

In many areas of surgical practice, it may be desirable to manipulate an internal organ without causing damage to the organ. In some circumstances, the surgeon may wish to turn, lift or otherwise reorient the organ so that surgery may be performed upon it. In other circumstances, the surgeon may simply want to move the organ out of the way. In still other cases, the surgeon may wish to hold the organ, or a portion of it, immobile so that it will not move during the surgical procedure.

Unfortunately, many organs are slippery and are difficult to manipulate. Holding an organ with the hands may be undesirable because of the slipperiness of the organ. Moreover, the surgeon's hands ordinarily cannot hold the organ and perform the procedure at the same time. The hands of an assistant may be bulky, becoming an obstacle to the surgeon. Also, manual support of an organ over an extended period of time can be difficult due to fatigue. Holding an organ with an instrument may damage the organ, especially if the organ is unduly squeezed, pinched or stretched. Holding an organ improperly may also adversely affect the functioning of the organ.

The heart is an organ that may be more effectively treated if it can be manipulated. Many forms of heart manipulation may be useful, including moving the heart within the chest and holding it in place. Some forms of heart disease, such as blockages of coronary vessels, may best be treated through procedures performed during open-heart surgery. During open-heart surgery, the patient is typically placed in the supine position. The surgeon performs a median sternotomy, incising and opening the patient's chest. Thereafter, the surgeon may employ a rib-spreader to spread the rib cage apart, and may incise the pericardial sac to obtain access to the heart. For some forms of open-heart surgery, the patient is placed on cardiopulmonary bypass (CPB) and the patient's heart is arrested. Stopping the patient's heart is a frequently chosen procedure, as many coronary procedures are difficult to perform if the heart continues to beat. CPB entails trauma to the patient, with attendant side effects and risks. An alternative to CPB involves operating on the heart while the heart continues to beat.

Once the surgeon has access to the heart, it may be necessary to lift the heart from the chest or turn it to obtain access to a particular region of interest. Such manipulations are often difficult tasks. The heart is a slippery organ, and it is a challenging task to grip it with a gloved hand or an instrument without causing damage to the heart. Held improperly, the heart may suffer ischemia, hematoma or other trauma. The heart may also suffer a loss of hemodynamic function, and as a result may not pump blood properly or efficiently. Held insecurely, the heart may drop back into the chest, which may cause trauma to the heart and may interfere with the progress of the operation.

SUMMARY

In general, the invention provides techniques for securely engaging an organ, such as a beating heart, with a manipulating device. The manipulating device that engages the organ may be, for example, a device that holds the organ with vacuum pressure. Some manipulating devices are at risk of disengaging from the organ, causing the organ to drop into the chest cavity. For example, a vacuum-assisted manipulation device may lose its hold on the organ when the vacuum fails.

The invention provides techniques for holding and engaging the organ more securely. The surgeon deploys a bag-like device around a substantial volume of the organ. In an exemplary embodiment, the bag-like device includes one or more mesh apertures, like a net. Prior to deployment, the bag-like device may have a rolled-up configuration like a stocking. The bag-like device may deployed by unrolling the bag-like device around the organ and the manipulating device.

Once the bag-like device is deployed, the organ may be lifted, turned or otherwise manipulated with the manipulating device and the bag-like device cooperating to manipulate the organ. In some cases, the bag-like device may be formed from materials that accommodate the natural motions of the organ. When deployed around a beating heart, the bag-like device may allow the heart to expand, contract, bob and twist. Further, bag-like device may be formed from materials that cause the device to adhere to the organ. In some circumstances, a drawstring may be used to help keep the bag-like device in place.

The bag-like device may have mesh apertures that make the device net-like. Mesh apertures may provide sufficient access to the organ for a surgeon to perform a procedure. When the surgeon needs access to a region of the organ covered by the bag-like device, the bag-like device may be cut to allow access to the organ, yet retain the structural integrity of the bag-like device. In this case, portion of the bag-like device that are not cut may remain substantially intact.

In one embodiment, the invention is directed to an apparatus comprising a manipulating device that contacts an organ and a bag-like device that extends around a substantial volume of the organ and the manipulating device. The bag-like device may include a center region that engages the manipulating device and a pliable netting near the perimeter. The netting may define mesh apertures that allow the surgeon to see the organ. The mesh apertures also aid the surgeon in cutting the bag-like device, if necessary.

In another embodiment, the invention presents a method, comprising engaging an organ with a manipulating device, deploying a bag-like device around a substantial volume of the organ and manipulating the organ with the manipulating device and the bag-like device. When the manipulating device is a vacuum-assisted device, the method may further include engaging the manipulating device with the organ to define a chamber and applying vacuum pressure to the chamber such that a portion of the manipulating device deforms to substantially seal the chamber against leakage.

In a further embodiment, the invention is directed to techniques for manipulating a heart. The method includes engaging a manipulating device with the apex of the heart to define a chamber, applying vacuum pressure to the chamber and deploying a bag-like device around the heart. The heart may be manipulated with the bag-like device.

The invention can provide one or more advantages. The bag-like device may reduce the risk that the organ may be inadvertently released or dropped. The bag-like device may thereby provide an extra measure of safety in the event the manipulating device should fail. In the case of deployment around a heart, the bag-like device accommodates the natural motions of the heart, maintaining the hemodynamic functions of the heart. The device is compact and easy to deploy, and can be easily removed with a cutting instrument such as a scissors.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
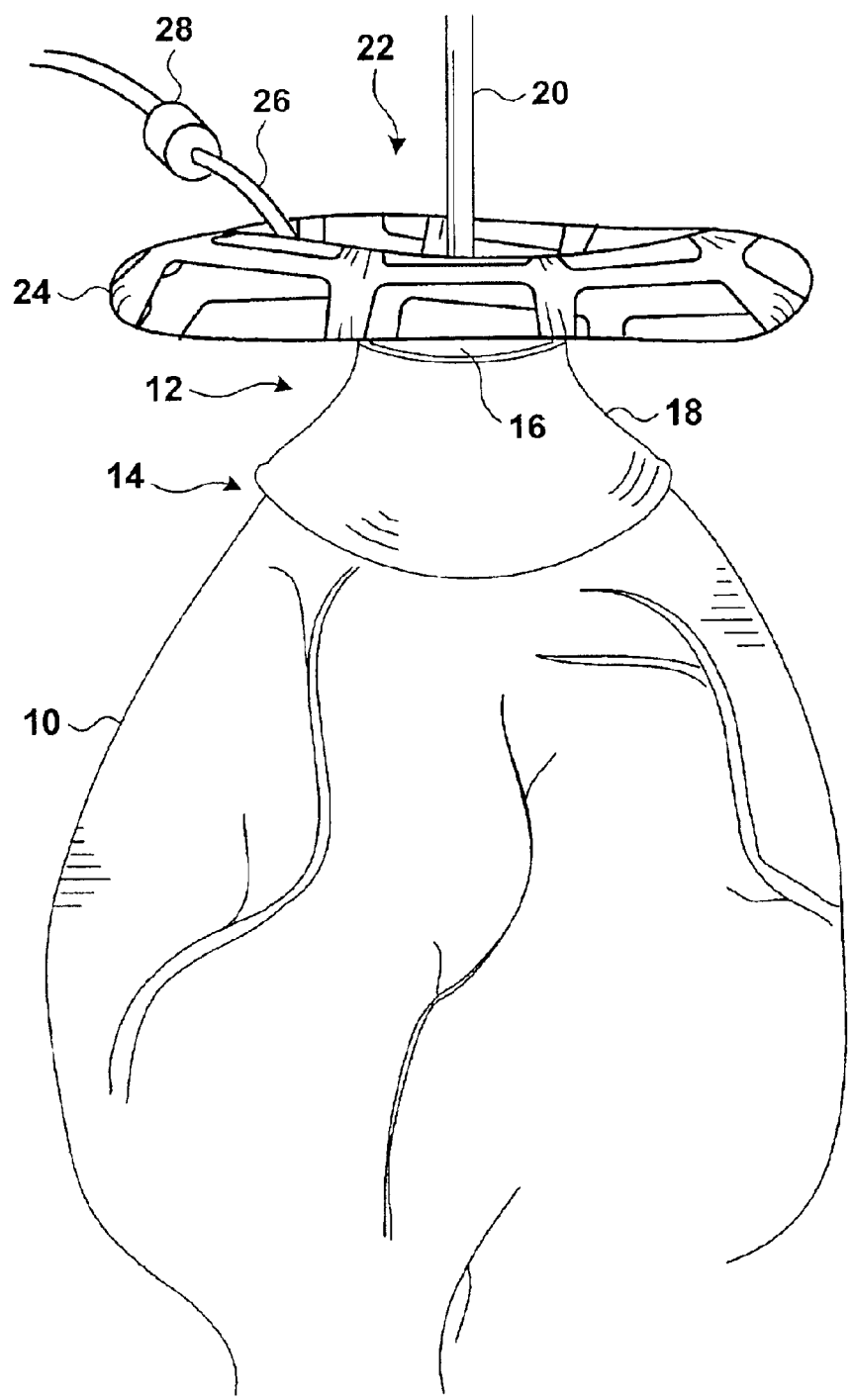
FIG. 1 is a perspective view of a manipulating device with a net-like device in an undeployed configuration, in conjunction with a beating heart.

FIG. 1 is a perspective view of a heart 10, which is being held by a manipulating device 12. In the exemplary application shown in FIG. 1, a surgeon (not shown in FIG. 1) has obtained access to heart 10 and has placed manipulating device 12 over the apex 14 of heart 10. The surgeon has lifted apex 14 with manipulating device 12 to obtain access to a desired region of heart 10.

Manipulating device 12 is an example of many possible devices that may engage heart 10 by apex 14. Exemplary manipulating device 12 of FIG. 1 is a device that forms a seal with the tissue of heart 10, assisted by vacuum pressure.

Manipulating device 12 includes a cup-like member 16 and a skirt-like member 18 extending outward from cup-like member 16. Manipulating device 12 adheres to apex 14 with the aid of vacuum pressure supplied from a vacuum source (not shown in FIG. 1) via a vacuum tube 20, which is coupled to cup-like member 16. Skirt-like member 10 deforms and substantially forms a seal against the surface of the tissue of heart 10. Skirt-like member 16 may be formed of a compliant material that promotes maintenance of the seal even as heart 10 beats. Adherence between heart 10 and manipulating device 12 may be promoted by other factors as well, such as a tacky surface of skirt-like member 18 placed in contact with heart 10.

Manipulating device 12 and vacuum tube 20 illustrate the practice of the invention. The invention is not limited to manipulating device 12, however. The invention may be practiced with a manipulating device that is not vacuum-assisted, or a manipulating device that is not cup-shaped, or a manipulating device that lacks a skirt-like member. The invention may be practiced with manipulating devices of any shape. For example, the invention may be practiced with a manipulating device that is irregularly shaped, including projections that extend radially outward from the center of the manipulating device and conform to the irregular shape of heart 10. In another context, the manipulating device may include a plurality of vacuum-assisted appliances, or the manipulating device may use no vacuum pressure at all.

In the exemplary application shown in FIG. 1, vacuum tube 20 serves as a support shaft for manipulating device 12 and as a supply of vacuum pressure. When manipulating device 12 is not vacuum-assisted, vacuum tube 20 may be replaced by a support shaft such as a plastic shaft. Alternatively, manipulating device 12 may be vacuum-assisted, but may be supported by a dedicated support shaft, with vacuum tube 20 providing little or no load-bearing support. The support shaft may be flexible. Manipulating device 12 and the support shaft may be coupled in any number of ways, such as by a fixed joint, a flexible joint or a swivel connection.

Vacuum tube 20 may be supported by a supporting arm (not shown), which may be affixed to a relatively immovable object, such as a rib spreader (not shown) or an operating table (not shown). In this manner, vacuum tube 20 may support manipulating device 12 to keep apex 14 elevated.

Although held by manipulating device 12, heart 10 has not been arrested and continues to beat. Beating causes heart 10 to move in three dimensions. In particular, heart 10 moves in translational fashion, by bobbing up and down and by moving from side to side. Heart 10 also expands and contracts as heart 10 fills with and expels blood. Heart 10 may twist as it expands and contracts. Although heart 10 may be securely held by manipulating device 12, there may be a risk that heart 10 will disengage from manipulating device 12. Disengagement may have any of a number of causes. The vacuum source may fail, for example. Also of concern is that the seal of skirt-like member 18 against the tissue of heart 10 may be accidentally broken, such as by twisting of heart 10 away from manipulating device 12, or by the surgeon trying to lift apex 14 too high.

To reduce the risk that heart 10 may disengage from manipulating device 12, the surgeon may deploy a bag-like device around heart 10. In FIG. 1, the bag-like device is embodied as a net-like device 22 including a pliable netting 24. Net-like device 22 and netting 24 may be fabricated from a variety of materials. In some embodiments, netting 24 may be formed from a flexible polymer such as silicone or urethane. Netting 24 may be generally soft, non-abrasive and biocompatible. Net-like device 22 may also include a drawstring 26 and a lock 28, which will be described in more detail below.

Figure 2:
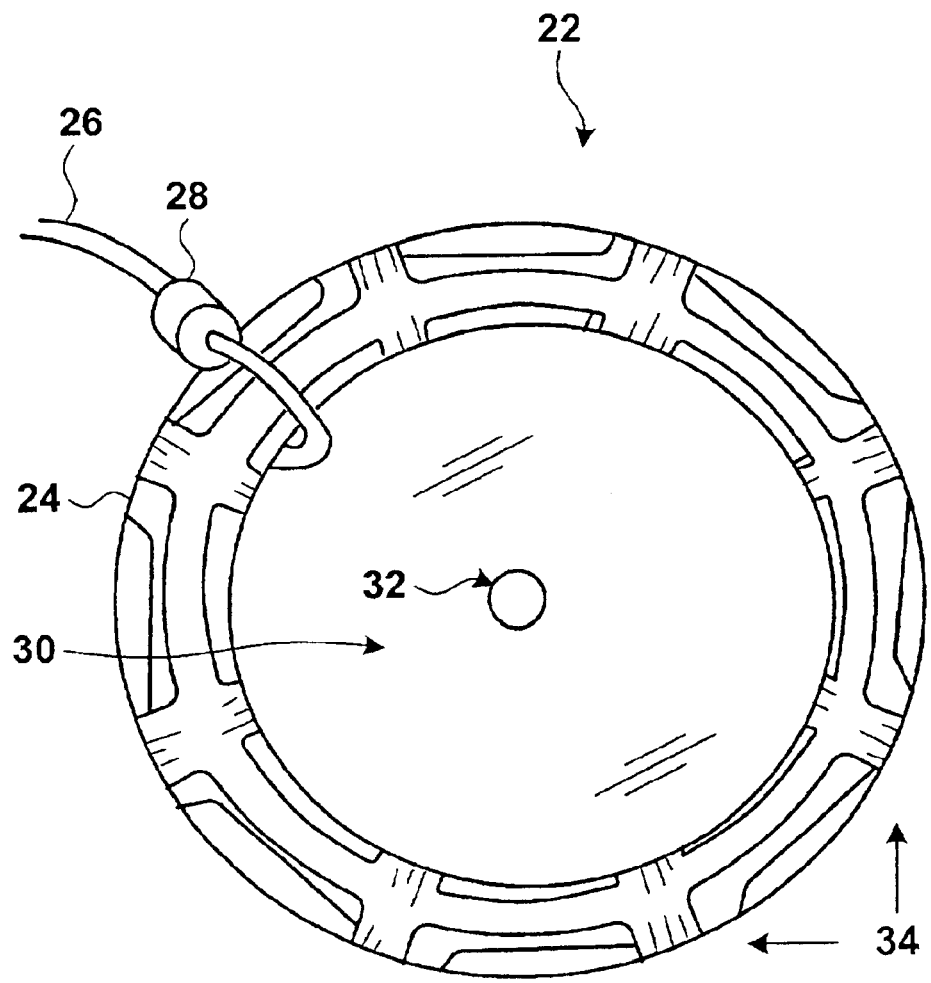
FIG. 2 is a plan view of the net-like device of FIG. 1 in an undeployed configuration.

In FIG. 1, net-like device 22 is shown prior to deployment. Likewise, FIG. 2 provides a plan view of net-like device 22 prior to deployment. A center region 30 of net-like device 22 may be constructed as a solid sheet of material, with an aperture 32. Aperture 32 can be made large enough to allow vacuum tube 20 (not shown in FIG. 2) to pass, but not large enough to allow manipulating device 12 (not shown in FIG. 2) to pass. In this manner, net-like device 22 remains generally anchored near the junction between vacuum tube 20 and cup-like member 16. In the case of a support shaft separate from vacuum tube 20, the center region 30 of net-like device 22 may include an aperture sized and shaped to accommodate both the support shaft and vacuum tube 20, or the center region 30 of net-like device 22 may include separate apertures to accommodate the support shaft and vacuum tube 20.

Netting 24, which is near the perimeter 34 of net-like device 22, can be rolled up much like a stocking. Net-like device 22 may be deployed by unrolling netting 24 around heart 10 (not shown in FIG. 2). The act of unrolling net-like device imparts little downward force on heart 10 and is unlikely to disengage heart 10 from manipulating device 12. Although rolling may provide convenience to the surgeon, netting 24 alternatively may be used in non-rolled configurations.

Manipulating device 12 and net-like device 22 may be assembled in many ways. For example, assembly may be accomplished by threading vacuum tube 20 through aperture 32, and coupling vacuum tube 20 to a vacuum source. Assembly may also be accomplished by threading vacuum tube 20 through aperture 32 and then coupling manipulating device 12 to vacuum tube 20 with a coupling mechanism. Net-like device 22 may be situated anywhere along vacuum tube 20 while in its undeployed configuration, and need not be proximal to manipulating device 12 as shown in FIG. 1.

Figure 3:
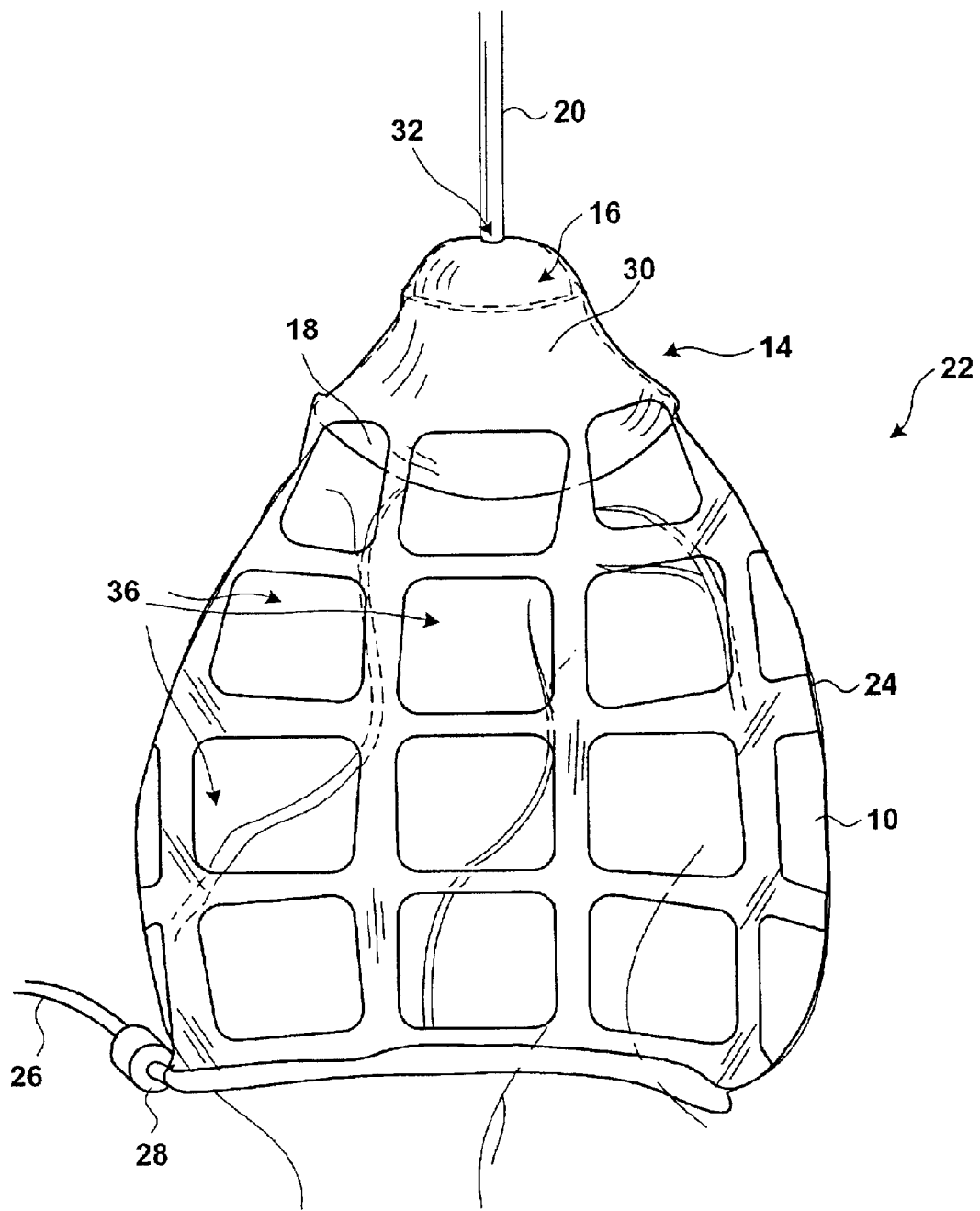
FIG. 3 is a perspective view of the manipulating device and the net-like device of FIG. 1 in an deployed configuration, in conjunction with a beating heart.

FIG. 3 shows net-like device 22 in a deployed position. In particular, netting 24 has been unrolled over heart 10. Net-like device 22 may be sized and shaped to surround a substantial volume of heart 10, including both ventricles and some of the atria as well. Drawstring 26 has been pulled snug and is held in place with lock 28. Lock 28 may be, for example, a clasp or a spring-loaded fastener. Drawstring has not been pulled so tight as to interfere with the contraction and expansion of heart 10 or the blood flow through the superior vena cava, inferior vena cava, pulmonary veins, pulmonary arteries or aorta (not shown). Drawstring 26 is shown for clarity as jutting away from heart 10, but in practice, drawstring 26 maybe positioned close to heart 10 or tucked away or cut off so that drawstring 26 will be out of the surgeon's way.

Net-like device 22 may be formed from an elastic material that permits stretching to accommodate the girth of heart 10. The flexible material of net-like device 22 accommodates the expanding and contracting of the beating heart. Pliable netting 24 may include a tacky material such as silicone gel that promotes adhesion between the tissue of heart 10 and netting 24. Adherence between netting 24 and the tissue may help prevent the tissue from chafing against netting 24. In addition, adherence aids netting 24 in engaging and supporting heart 10.

Net-like device 22 also engages manipulating device 12. Vacuum tube 20 passes through aperture 32, but center region 30 drapes over manipulating device 12. The flexible material of net-like device 22 accommodates the movement of manipulating device 12, which may be coupled to vacuum tube 20 with a flexible coupling such as a swivel joint.

When net-like device 22 is deployed, heart 10 may be lifted, supported, turned, moved or otherwise manipulated. Manipulating device 12 and net-like device 22 may cooperate to make manipulation safer and more effective. When heart 10 is supported by apex 14 as shown in FIG. 3, for example, heart 10 is supported in two ways. First, manipulating device 12 adheres to apex 14 with the aid of vacuum pressure. Second, manipulating device 12 supports net-like device 22, which in turn supports heart 10. In this manner, manipulating device 12 and net-like device 22 cooperate to provide safer and more effective support than manipulating device 12 alone. In case the vacuum supply should fail or the seal of skirt-like member 18 against the tissue of heart 10 should be accidentally broken, net-like device 22 will prevent heart 10 from dropping back into the chest cavity. Preventing heart 10 from moving unexpectedly is important in delicate surgical procedures such as coronary bypass procedures.

Netting 24 may define several mesh apertures, such as those identified with reference numeral 36. Mesh apertures 36 can be large, so that the surgeon may easily identify structures on the surface of heart 10. The invention is not limited to netting 24 with mesh apertures 36 of the size and shape depicted in FIG. 3. The invention encompasses netting with mesh apertures of any shape and size. The invention also encompasses devices having no visible mesh apertures, which may resemble a bag more than a net. The bag-like device may be constructed of translucent or transparent material that allows the surgeon to identify structures on the surface of heart 10.

Figure 4:
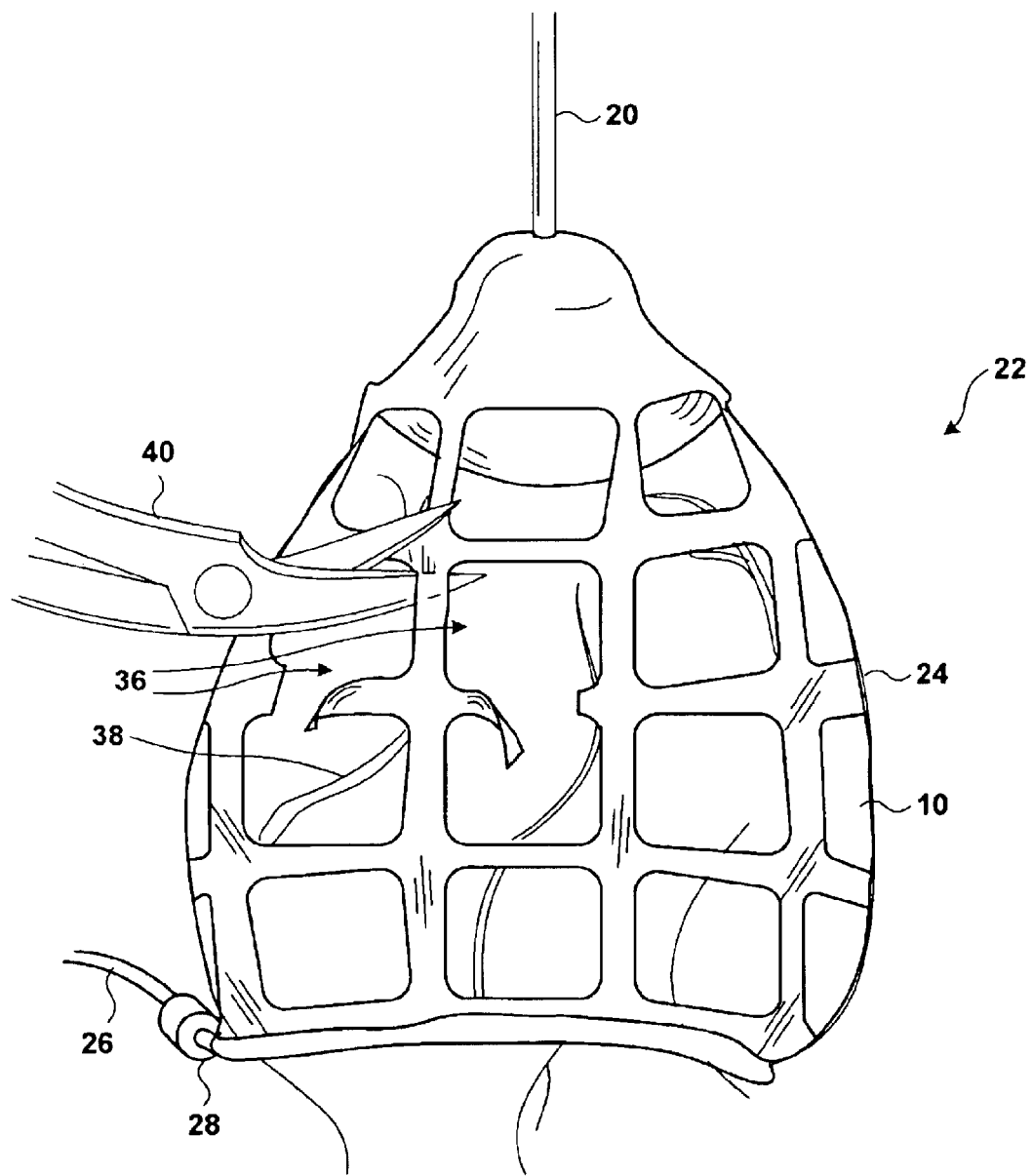
FIG. 4 shows the net-like device being cut in an exemplary application.

FIG. 4 shows an embodiment of the invention in a typical application. In a procedure such as a coronary bypass procedure, the surgeon may need to lift and turn heart 10 to obtain access to a particular region of interest, such as a blocked coronary artery 38. Netting 24, however, may prevent access to artery 38. The surgeon may obtain access to artery 38, however, by cutting through netting 24 with a scissors 40 to expose the region of interest. Large mesh apertures 36 accommodate scissors 40 and allow the surgeon to expose a region of heart 10 with a few cuts. Although netting 24 may be cut, net-like device 22 may retain most of its structural integrity in uncut regions and may continue to support heart 10.

Following completion of the surgical procedure, the surgeon removes netlike device 22. The surgeon may loosen drawstring 26 and cut away netting 24 with scissors 40. Net-like device 22 may be peeled away from the tissue, and heart 10 may be lowered back to the chest cavity with manipulating device 12. Manipulating device 12 may be disengaged from apex 14, and manipulating device 12 and the remnants of net-like device 22 may be removed from the operating field.

FIGS. 1 through 4 depict one embodiment of a bag-like device, i.e., a net-like device. As noted above, the invention is not limited to bag-like devices that are also net-like. The bag-like device may have no mesh apertures at all, or may have mesh apertures considerably smaller than depicted in the figures. The mesh apertures may be differently shaped and spaced than depicted in the figures. For example, the netting may include circular mesh apertures arrayed in a honeycomb configuration. The mesh apertures need not have uniform sizes or shapes. The netting need not have apertures at all sites. For example, the bag-like device may include a plurality of mesh apertures on the anterior side of the bag-like device and no mesh apertures on the posterior side. The invention encompasses all of these variations.

Mesh apertures may provide a number of advantages, however. Mesh apertures may make it easier for the surgeon to see the surface of the organ. In heart surgery, for example, being able to see the surface of the heart may be important to the surgeon. In addition, mesh apertures facilitate cutting as depicted in FIG. 4.

The invention can provide one or more additional advantages. The bag-like device can be simple to deploy and can be deployed in a matter of seconds. Once deployed, the bag-like device may be adjusted for a secure placement, such as by adjusting a drawstring and a lock. The bag-like device may conform to the shape of the organ, thereby taking up little space in the operating field.

The bag-like device cooperates with the manipulating device in manipulating the organ. The bag-like device further provides an extra measure of safety in the event the manipulating device should fail. In the case of heart surgery, the bag-like device provides the functionality and safety without compromising the hemodynamic functions of the heart.

More than one bag-like device may be used with a single manipulating device. In an undeployed configuration such as is depicted in FIGS. 1 and 2, bag-like devices are compact and easily manageable. Several bag-like devices may be used in a single procedure. A surgeon performing a multiple bypass procedure, for example, may thread the vacuum tube and/or support shaft through the apertures of two bag-like devices. In the course of performing the first bypass, the surgeon may cut away pieces of the first bag-like device, as shown in FIG. 4. The second bypass, however, may need to be performed at another site of the heart, and further cutting of the first bag-like device may compromise its structural integrity. Accordingly, the surgeon may cut away the first bag-like device and deploy the second around the heart.

Furthermore, the bag-like device may be used with multiple manipulation devices. In heart surgery, for example, the bag-like device may cooperate with a manipulating device that lifts the heart by the apex. Other manipulation devices may also be brought in contact with the heart. For example, an instrument to stabilize or immobilize a region of the heart may be placed in contact with the heart and the bag-like device.

Various embodiments of the invention have been described. These embodiments are illustrative of the practice of the invention. Various modifications may be made without departing from the scope of the claims. For example, the bag-like device is not limited to use with a heart, but may be adapted for use with other organs. Sizes and shapes of bag-like devices may vary, depending on the organ to be held with a device. The bag-like device may be deployed to extend around a substantial volume of the organ using techniques other than unrolling. For example, the bag-like device may be pulled like a sleeve over the organ, or the bag-like device may be unfolded over the organ or the bag-like device may be wrapped around the organ. The bag-like device may be secured using techniques other than pulling a drawstring.

Deploying a bag-like device around a substantial volume of the organ does not necessarily require deployment about the entire organ or a majority of the volume of the organ. Rather, the affected volume of the organ may depend upon the particular organ involved. Deployment of a bag-like device around a section of an intestine, for example, may allow the section to be supported, moved, lifted, twisted or otherwise manipulated with the manipulating device and/or the bag-like device. The bag-like device may extend around a substantial volume of the intestine even though most of the intestine may be unaffected by the manipulating device or the bag-like device.

The bag-like device may be formed from a single material or from a plurality of materials. A bag-like device may include a center region formed from nonflexible materials, for example, and a netting of woven flexible filaments. These and other embodiments are within the scope of the following claims.

What is claimed is:

1. A method comprising:
   engaging a manipulating device with the apex of the heart to define a chamber;
   applying vacuum pressure to the chamber; and
   deploying a bag-like device around at least a portion of the heart, the bag-like device comprising a netting having at least one mesh aperture.

2. The method of claim 1, further comprising manipulating the heart with the bag-like device.

3. The method of claim 2, wherein manipulating the heart comprises lifting the heart.

4. The method of claim 1, further comprising securing the bag-like device around the heart.

5. The method of claim 4, wherein securing the bag-like device around the heart comprises pulling a drawstring.

6. The method of claim 5, further comprising constricting one end of the bag-like device by pulling the drawstring.

7. The method of claim 1, wherein deploying the bag-like device around the heart comprises unrolling the bag-like device.

8. The method of claim 1, further comprising:
   threading a vacuum tube through an aperture in the bag-like device; and
   applying vacuum pressure to the chamber through the vacuum tube.

9. The method of claim 1, further comprising cutting the bag-like device to expose a region of the heart.

10. The method of claim 9, wherein cutting the bag-like device comprises insertion of at least part of a cutting instrument into the mesh aperture of the bag-like device.

11. The method of claim 1, further comprising cutting the bag-like device to remove the bag-like device from around the heart.

12. The method of claim 1, wherein deploying the bag-like device comprises deploying the bag-like device after engaging the manipulating device with the apex of the heart.

13. An apparatus comprising:
   a manipulating device that contacts an organ; and
   a bag-like device comprising a netting having at least one mesh aperture that is adapted to extends around a substantial volume of the organ and the manipulating device.

14. The apparatus of claim 13, the bag-like device comprising a pliable netting.

15. The apparatus of claim 13, the bag-like device comprising a center region that engages the manipulating device.

16. The apparatus of claim 13, the bag-like device comprising a center region and a perimeter, the perimeter comprising a pliable netting and a drawstring.

17. The apparatus of claim 13, wherein the bag-like device is formed from a flexible polymer.

18. The apparatus of claim 13, further comprising a support shaft coupled to the manipulating device.

19. The apparatus of claim 18, the support shaft comprising a vacuum tube.

20. The apparatus of claim 18, the bag-like device further comprising an aperture sized to permit passage of the support shaft and sized to block passage of the manipulating device.

21. A method comprising:
   engaging an organ with a manipulating device;
   deploying a bag-like device around a substantial volume of the organ; and
   manipulating the organ with the manipulating device and the bag-like device.

22. The method of claim 21, wherein engaging the organ with the manipulating device comprises:
   engaging the manipulating device with the organ to define a chamber; and
   applying vacuum pressure to the chamber such that a portion of the manipulating device deforms to substantially seal the chamber against leakage.

23. The method of claim 21, wherein manipulating the organ comprises at least one of lifting, supporting, twisting and moving the organ.

24. The method of claim 21, further comprising securing the bag-like device around the organ.

25. The method of claim 21, wherein deploying the bag-like device comprises unrolling the bag-like device.

26. The method of claim 21, further comprising cutting the bag-like device.

27. The method of claim 21, wherein deploying the bag-like device comprises deploying the bag-like device after engaging the organ with the manipulating device.

* * * * *